US011103209B2

(12) United States Patent
Zhang et al.

(10) Patent No.: US 11,103,209 B2
(45) Date of Patent: Aug. 31, 2021

(54) ULTRASONIC SYSTEM AND METHOD FOR DETECTING A BIOFILM ON A TOOTH

(71) Applicant: Colgate-Palmolive Company, New York, NY (US)

(72) Inventors: Xiaonan Zhang, Hillsborough, NJ (US); Alan Sorrentino, Cranbury, NJ (US); Carlo Daep, Brooklyn, NY (US); Zi Wu, Ashburn, VA (US)

(73) Assignee: Colgate-Palmolive Company, New York, NY (US)

( * ) Notice: Subject to any disclaimer, the term of this patent is extended or adjusted under 35 U.S.C. 154(b) by 317 days.

(21) Appl. No.: 16/186,639

(22) Filed: Nov. 12, 2018

(65) Prior Publication Data

US 2019/0142365 A1 May 16, 2019

Related U.S. Application Data (60) Provisional application No. 62/587,006, filed on Nov. 16, 2017.

(51) Int. Cl.
*A61B 8/08* (2006.01)
*A61C 17/22* (2006.01)
(Continued)

(52) U.S. Cl.
CPC .................. *A61B 8/08* (2013.01); *A46B 9/04* (2013.01); *A46B 15/0002* (2013.01); *A61B 5/00* (2013.01);
(Continued)

(58) Field of Classification Search
CPC .... A61B 8/08; A61B 5/00; A61B 8/12; A61B 8/4444; A61B 8/4472; A61B 8/5207;
(Continued)

(56) References Cited

U.S. PATENT DOCUMENTS

| 5,369,831 A | * | 12/1994 | Bock | A46B 7/04 |
| | | | | 15/167.1 |
| 5,874,677 A | * | 2/1999 | Bab | A61C 19/04 |
| | | | | 73/629 |

(Continued)

FOREIGN PATENT DOCUMENTS

| CN | 2621627 | 6/2004 |
| CN | 101820832 | 9/2010 |

(Continued)

OTHER PUBLICATIONS

International Search Report and the Written Opinion of the International Searching Authority issued in international application PCT/US2018/060239 dated Feb. 12, 2019.

*Primary Examiner* — Dung Van Nguyen (57) ABSTRACT

An ultrasonic system may include: an oral care device including: a head; a plurality of teeth cleaning elements extending from a first side of the head; and an ultrasound module including an ultrasound transceiver positioned in the head, the ultrasound transceiver configured to produce an ultrasound signal on the first side of the head and to generate a detection signal from a reflected ultrasound signal; and a processing module operably coupled to the ultrasound module to receive the detection signal; wherein the processing module includes a programmable processor configured to process the detection signal non-linearly with respect to time by first identifying a first reflection representing a surface of a tooth and then determining whether a second reflection peak is present in the detection signal at a time prior to the first reflection peak, the second reflection peak representing a biofilm on the surface of the tooth.

20 Claims, 10 Drawing Sheets

(51) Int. Cl.
*A61B 8/12* (2006.01)
*A61B 8/00* (2006.01)
*A46B 9/04* (2006.01)
*A61B 5/00* (2006.01)
*A46B 15/00* (2006.01)

(52) U.S. Cl.
CPC .............. *A61B 5/0082* (2013.01); *A61B 8/12* (2013.01); *A61B 8/4444* (2013.01); *A61B 8/4472* (2013.01); *A61B 8/5207* (2013.01); *A61B 8/5223* (2013.01); *A61B 8/56* (2013.01); *A61C 17/22* (2013.01); *A46B 2200/1066* (2013.01); *A61B 8/0858* (2013.01); *A61B 8/0875* (2013.01)

(58) Field of Classification Search
CPC ..... A61B 8/5223; A61B 8/56; A61B 8/80858; A61B 8/0875; A46B 9/04; A46B 5/0002
See application file for complete search history.

(56) References Cited

U.S. PATENT DOCUMENTS

| | | | |
|---|---|---|---|
| 6,607,387 | B2 | 8/2003 | Mault |
| 6,949,072 | B2 | 9/2005 | Furnish et al. |
| 8,747,005 | B2* | 6/2014 | Kemp ...................... A61K 8/22 401/132 |
| 2006/0191086 | A1* | 8/2006 | Mourad ............. A46B 15/0028 15/22.1 |
| 2010/0198081 | A1 | 8/2010 | Hanlin et al. |
| 2011/0076638 | A1 | 3/2011 | Gottenbos et al. |
| 2012/0295216 | A1 | 11/2012 | Dykes et al. |
| 2018/0177489 | A1* | 6/2018 | Yu ........................ A61B 8/5223 |

FOREIGN PATENT DOCUMENTS

| | | |
|---|---|---|
| CN | 205513152 | 8/2016 |
| WO | 2014/097022 | 6/2014 |

* cited by examiner

ULTRASONIC SYSTEM AND METHOD FOR DETECTING A BIOFILM ON A TOOTH

BACKGROUND

One of the most common oral health problems, and one that has an easy to manage solution, is the presence of plaque on tooth enamel. Dental plaque is a biofilm that is known as the primary cause of dental caries and other oral infections, which can lead to damaged teeth, tooth decay, or even tooth loss. If dental plaque isn't removed when it is soft, it can harden and become more difficult to remove. Methods have therefore been developed for the early detection of dental plaque.

One method uses dyes to color stain the biofilm so that it can be seen and removed, but this method can leave the dye on the teeth for an extended period of time. Another dye method uses a type of dye which is visible under ultraviolet light, and while this method does not leave the teeth visibly dyed, because the biofilm is only visible under ultraviolet light, the cleaning process becomes more difficult for an individual without assistance. Imaging methods, such as ultrasonography and optical coherence tomography, may also be used for detecting the presence of a biofilm on teeth. These methods may be used to first produce images of the surface of the teeth, and from the images a determination may be made about the presence of a biofilm. And, while the image analysis process may be amenable to automation, such image analysis can require high processing overhead and/or professional in order to detect the biofilm layer. These imaging methods, because of their complexity and costs, are not generally available to the individual user.

In view of the impracticality of existing biofilm detection systems and methods, there is a need for a cost-effective and easy to use system and method that can readily be used for personal biofilm detection. Such a system and method can serve to improve the overall oral health of individuals.

BRIEF SUMMARY

Exemplary embodiments according to the present disclosure are directed to ultrasonic systems and methods which may be used to detect the presence of a biofilm on the surface of a tooth. The ultrasonic system employs an oral care device and a processing module. The oral care device has a head, teeth cleaning elements extending from the head, and an ultrasound module with an ultrasound transceiver positioned in the head. The processing module receives a detection signal from the ultrasound transceiver, and while the user is brushing their teeth, the processing module is able to determine in real time whether a biofilm is present on the surface of a tooth or teeth in contact with the teeth cleaning elements. The processing module accomplishes this detection efficiently by processing the detection signal in a non-linear manner with respect to time. The system may also be used to continuously detect a biofilm on the surface of teeth and provide feedback in real time as the user brushes their teeth. The ultrasonic method includes steps of placing the head of an oral care device adjacent teeth, with the head including an ultrasound transceiver, generating a detection signal using the ultrasound transceiver, and then processing the detection signal in a non-linear manner with respect to time. The method may also include providing real time feedback to the user while the user brushes their teeth.

In one aspect, the invention can be an ultrasonic system including: an oral care device including: a head; a plurality of teeth cleaning elements extending from a first side of the head; and an ultrasound module including an ultrasound transceiver positioned in the head, the ultrasound transceiver configured to produce an ultrasound signal on the first side of the head and to generate a detection signal from a reflected ultrasound signal; and a processing module operably coupled to the ultrasound module to receive the detection signal; wherein the processing module includes a programmable processor configured to process the detection signal non-linearly with respect to time by first identifying a first reflection representing a surface of a tooth and then determining whether a second reflection peak is present in the detection signal at a time prior to the first reflection peak, the second reflection peak representing a biofilm on the surface of the tooth.

In still another aspect, the invention can be an ultrasonic method for detecting a biofilm on a surface of a tooth, the method including: placing a head of an oral care device adjacent the surface of the tooth, the oral care device including a plurality of teeth cleaning elements extending from a first side of the head, such that the plurality of teeth cleaning elements are between the head and the surface of the tooth, and an ultrasound module including an ultrasound transceiver positioned in the head; generating a detection signal using the ultrasound transceiver by directing an ultrasound signal from the first side of the head toward the tooth and receiving a reflected ultrasound signal, the detection signal being generated from the reflected ultrasound signal; and processing, using a processing module, the detection signal non-linearly with respect to time by first identifying a first reflection representing a surface of a tooth and then determining whether a second reflection peak is present in the detection signal at a time prior to the first reflection peak, the second reflection peak representing a biofilm on the surface of the tooth.

In yet another aspect, the invention can be an ultrasonic method for detecting a biofilm on a surface of teeth, the method including: moving a head of an oral care device along the surface of the teeth within an oral cavity, the oral care device including a plurality of teeth cleaning elements extending from a first side of the head, such that the plurality of teeth cleaning elements are between the head and the surface of the teeth, and an ultrasound module including an ultrasound transceiver positioned in the head; generating a detection signal using the ultrasound transceiver while moving the head, the ultrasound transceiver directing an ultrasound signal from the first side of the head toward the tooth and receiving a reflected ultrasound signal, the detection signal being generated from the reflected ultrasound signal; identifying a first reflection peak at a first time in the detection signal, using a processing module and while moving the head, the first reflection peak representing the surface of the teeth; determining whether a second reflection peak is present in the detection signal within a first predetermined time period before the first time, using a processing module and while moving the head, such that the second reflection peak and the first reflection peak have an amplitude ratio approximately equal to a previously calculated amplitude ratio, the second reflection peak representing a bio film on the surface of the tooth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof. The computer programmable processes may be executed on a single processor or on or across multiple processors.

Processors described herein may be any central processing unit (CPU), microprocessor, micro-controller, computational, or programmable device or circuit configured for executing computer program instructions (e.g. code). Various processors may be embodied in computer and/or server hardware and/or computing device of any suitable type (e.g. desktop, laptop, notebook, tablet, cellular phone, smart phone, PDA, etc.) and may include all the usual ancillary components necessary to form a functional data processing device including without limitation a bus, software and data storage such as volatile and non-volatile memory, input/output devices, a display screen, graphical user interfaces (GUIs), removable data storage, and wired and/or wireless communication interface devices including Wi-Fi, Bluetooth, LAN, etc.

Computer-executable instructions or programs (e.g. software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs is referred to hereinafter as a "programmable device", or just a "device" for short, and multiple programmable devices in mutual communication is referred to as a "programmable system". It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Figure 1A:
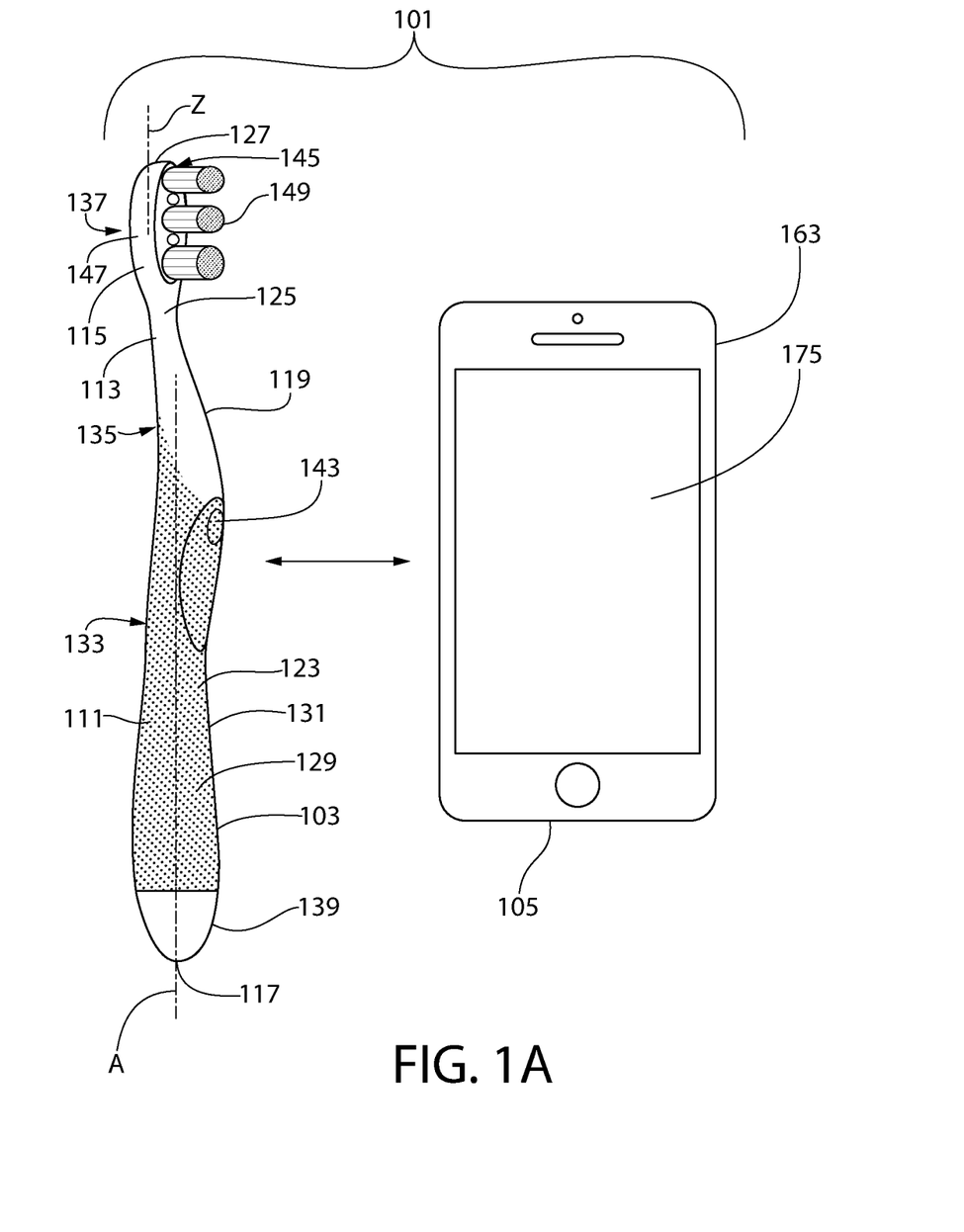
FIG. 1A illustrates an ultrasonic system in accordance with a first embodiment of the present invention.

Turning in detail to the drawings, FIG. 1A illustrates an ultrasonic system 101 in accordance with an embodiment of the present invention. The ultrasonic system 101 includes an oral care device 103 and a processing module 105. The oral care device 103 generally includes a handle 111, a neck 113, and a head 115. The neck 113 extends between the handle 111 and the head 115 and connects the head 115 to the handle 111. Although the oral care device 103 is shown as a toothbrush, the invention is not to be so limited unless otherwise stated in the claims.

The handle 111 provides the user with a mechanism by which the oral care device 103 can be readily gripped and manipulated during a brushing regimen. The handle 111 may be formed of many different shapes, sizes and materials and may be formed by a variety of manufacturing methods that are well-known to those skilled in the art. The handle 111 extends from a proximal end 117 to a distal end 119 to along a longitudinal axis A to form an elongated gripping portion 123 therebetween. The handle 111 transitions into the neck 113 at the distal end 119 of the handle 111. While the head 115 is normally widened relative to the neck 113, in some constructions the head 115 can simply be a continuous extension or narrowing of the neck 113 and/or handle 111. While the neck 113 generally has a smaller transverse cross-sectional area than the handle 111, the invention is not so limited. Broadly speaking, the neck 113 forms a transition region between the handle 111 and the head 115, with the head 115 extending from an end of the neck 113 opposite the handle 111. The head 115 extends from a proximal end 125 to a distal end 127 along a z-axis. In the exemplary embodiment, the z-axis is parallel to the longitudinal axis A. In certain embodiments, the z-axis may be placed at an angle to the longitudinal axis A.

In the exemplary embodiment, the handle 111 includes a suitable textured grip 129 made of a soft elastomeric material. The textured grip 129 may cover at least a portion of a front surface 131 and a rear surface 133 of the handle 111. The textured grip 129 may also extend to a rear surface 135 of the neck 113 and to a rear surface 137 of the head 115. The handle also includes a removable end cap 139 which enables access into a cavity 141 formed within the handle 111.

In embodiments in which a portion of the front surface 131 of the handle 111 is also covered by or formed from the material of the textured grip 129, the textured grip 129 may form part of or cover an electrical switch 143, which is operable between an open state and a closed state. The open and closed states of the electrical switch 143 serve to disconnect and connect, respectively, electric power to electronic circuitry (described below) within the handle 111. In certain embodiments, the electrical switch 143 may be a single button which alternates between the open and closed states. In alternative embodiments, the electrical switch 143 may include multiple buttons which serve to control the switch between the open and closed states. Of course, other types of switches may be used in conjunction with the oral care device 103 for activating and deactivating the electronic circuitry within the handle 111, including without limitation slide switches, toggle switches, motion activated switches, photo-sensitive switches, sound-activated switches, electronic switches, and/or combinations thereof.

The electrical switch 143 may form one or more minor protrusions in the front surface 131 of the handle 111 for easy manipulation by a user. Specifically, when a user holds the oral care device 103 in a normal fashion, the user's thumb will be positioned adjacent the electrical switch 143 to easily enable the user to actuate the electrical switch 143 between the open and closed states as desired. Of course, the invention is not so limited and the electrical switch 143 may be otherwise located on the handle 111, the neck 113 or elsewhere on the oral care device 103.

The handle 111, the neck 113, and the head 115 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. However, in other embodiments, the handle 111, the neck 113, and the head 115 of the oral care device 103 may formed as a single unitary structure using a molding, milling, machining or other suitable process. Whether the handle 111, the neck 113, and the head 115 are of a unitary or multi-piece construction (including connection techniques) is not limiting of the present invention, unless specifically set forth in a claim. In some embodiments of the invention, the head 115 may be detachable (and replaceable) from the handle 111 and/or from the neck 113 using techniques known in the art.

The head 115 generally includes a front surface 145, the rear surface 137 and peripheral side surfaces 147 that extend between the front and rear surfaces 145, 137. The front surface 145 and the rear surface 137 of the head 115 can take on a wide variety of shapes and contours, none of which are limiting of the present invention. For example, the front and rear surfaces 145, 137 can be planar, contoured or combinations thereof.

The front surface 145 of the head 115 includes a collection of at least one teeth cleaning element, shown in the exemplary embodiment as a plurality of bristles 149, extending therefrom for cleaning teeth surfaces. As used herein, the term "teeth cleaning element" is used in a generic sense to refer to any structure that can be used to clean or polish the teeth through relative surface contact. In certain embodiments, the head 115 may include a single teeth cleaning element, and in other embodiments, the head 115 may include two or more teeth cleaning elements. Common examples of the at least one teeth cleaning element include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the at least one teeth cleaning element may be an elastomeric material having a hardness property in the range of A8 to A25 Shore hardness. Other materials within and outside the noted hardness range could also be used.

The bristles 149 of the present invention can be connected to the head 115 in any manner known in the art. For example, staples/anchors, in-mold tufting (IMT) or anchor free tufting (AFT) could be used to mount the bristles 149 of the exemplary embodiment. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Alternatively, the bristles could be mounted to tuft blocks or sections by extending through suitable openings in the tuft blocks so that the base of the bristles are mounted within or below the tuft block.

Figure 1B:
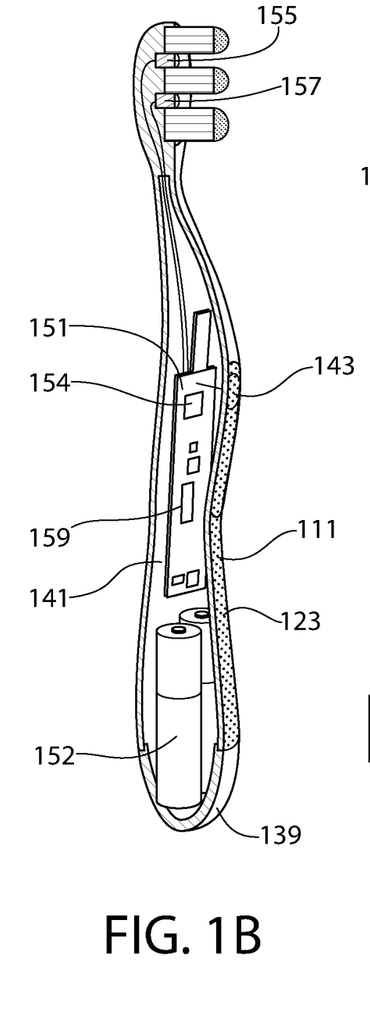
FIG. 1B illustrates the head of the toothbrush of FIG. 1A positioned against teeth.

Referring to FIG. 1B, the handle 111 is a housing for containing electronic circuitry 151 and a power source 152. The handle 111 is a hollow structure having a cavity 141 formed therein. More specifically, in the exemplified embodiment, the cavity 141 is formed in the elongated gripping portion 123 of the handle 111. In the exemplary embodiment, the power source 152 is shown as two batteries located within the handle 111. Of course, the invention is not so limited and more or fewer than two batteries may be used, or alternatively, other types of power sources may be used. A removable end cap 139 forms the proximal end 117 of the handle 111 by engagement with the gripping portion 123 of the handle 111. In the exemplary embodiment, the end cap 139 may threadably engage the gripping portion 123 of the handle 111. In other embodiments, the end cap 139 may engage the gripping portion 123 of the handle 111 by snap engagement or by any other mechanical locking engagement. Removal of the end cap 139 exposes an opening 159 which forms a passageway into the cavity 141 through which the power source 152 can be inserted into and removed from the cavity 141. Access to the cavity may be formed in other ways in other embodiments. For example, the handle 111 may include a sliding panel which is removable to form an elongated opening along the longitudinal axis A of the handle 111 (e.g., the front surface, the rear surface and/or the side surfaces) to provide access to the cavity 141. Prior to use, a user may insert the power source 152 through the opening 159 and into the cavity 141 in the elongated gripping portion 123 of the handle 111, and the cavity 141 is enclosed by replacing the end cap 139.

Figure 1C:
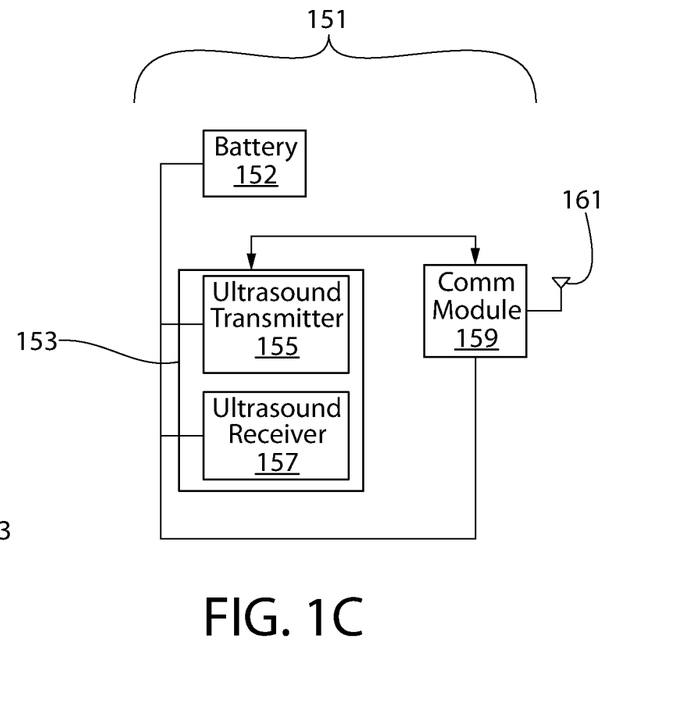
FIG. 1C schematically illustrates the electronic components of the toothbrush of FIG. 1B.

The electronic circuitry 151 which may be included in an exemplary oral care device 103 is shown in FIG. 1C. The electronic circuitry 151 includes an ultrasound module 152 communicably coupled to a communication module 159. The ultrasound module 152 includes a controller circuit 153, an ultrasound transmitter 155 and an ultrasound receiver 157. The controller circuit 153 controls operation of both the ultrasound transmitter 155 and the ultrasound receiver 157. In the embodiment shown, the ultrasound module 152 includes an ultrasound transmitter 155 that is separate from an ultrasound receiver 157, and in combination the two components form an ultrasound transceiver. In certain other embodiments, the ultrasound transmitter 155 and the ultrasound receiver 157 may be integrated into a single unit to form an ultrasound transceiver. In still other embodiments, the functional aspects of the ultrasound transmitter 155 and the ultrasound transceiver 157 may be combined to form an ultrasound transceiver. The ultrasound module 152 operates in accordance with well-known principals of ultrasonography, in which an ultrasound signal is generated by the ultrasound transmitter 155 and a reflected ultrasound signal is received by the ultrasound receiver 157. The ultrasound module 152 generates a detection signal from the reflected ultrasound signal. As is understood in the art, the detection signal includes one or more peaks which are representative of the structure in a tooth that reflects the ultrasound signal.

The communication module 159 in the exemplary embodiment includes an antenna 161 to enable wireless transmission. The communication module 159 may include an analog to digital converter to convert the detection signal into a digital form that is appropriate for wireless transmission. In certain embodiments, an analogue to digital converter may be included as part of the electronic circuitry 151 of the toothbrush separate from the communication module 159. The communication module 159 may be configured and/or programmed to communicate using a wireless technology standard such as Wi-Fi, Bluetooth®, and the like, or it may communicate using any type of proprietary wireless transmission protocol. In certain embodiments, the communication module 159 may include a port to enable communications using wired protocols, such as USB and the like.

Figure 1D:
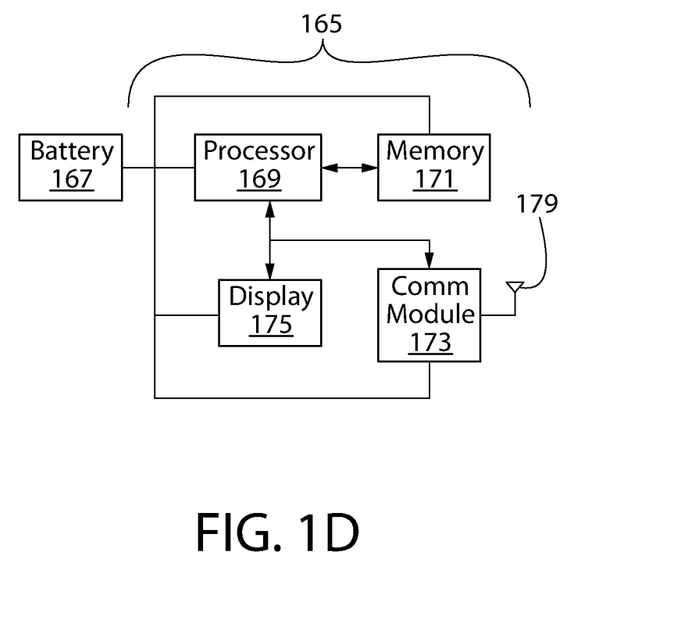
FIG. 1D schematically illustrates a processing module of the ultrasonic system of FIG. 1A.

Referring to both FIGS. 1A and 1D, the processing module 105 includes a housing 163 and electronic circuitry 165, with the housing enclosing and/or supporting the various components of the electronic circuitry 165. The electronic circuitry 165 is coupled to a power source 167, shown as a battery, and includes a processor 169 communicably coupled to a memory 171, a communication module 173, and a display 175. In certain embodiments, the electronic circuitry 165 may include other components, such as a speaker to provide audible feedback to the user, one or more buttons to receive input from the user, and one or more ports for making a wired connection between the electronic circuitry 165 and other external circuitry. In certain other embodiments, the processing module 105 may be a smartphone, a tablet computer, a laptop computer, and the like. The memory 171 may be any appropriate type of memory or storage which enables the processor 169 to perform the desired programming, such as volatile and/or non-volatile random access memory. The display 175 may be any type of light emitting display. As shown in the exemplary embodiment, the display 175 is an LED panel. In certain other embodiments, the display 175 may be an LCD panel, an OLED panel, or any other similar type of display which is electronically controllable by the processor 169 for providing visual feedback to the user. In certain embodiments, the display 175 may be a touch sensitive display which accepts input from the user directly on the display surface. The type and configuration of the display 175 is not to be limiting of the invention unless otherwise indicated in the claims. The communication module 173 includes an antenna 179 to enable wireless communication. The communication module 173 may be configured and/or programmed to communicate using a wireless technology standard such as Wi-Fi, Bluetooth®, and the like, or it may communicate using any type of proprietary wireless transmission protocol. The mode of communication for which the communication module 173 is configured is not to be limiting of the invention unless otherwise indicated in the claims. In certain embodiments, the communication module 173 may include a port to enable communications using wired protocols, such as USB and the like. For proper functioning of the exemplary embodiment, the communication module 159 of the oral care device 103 and the communication module 173 of the processing module 105 communicate with each other, whether such communications are wireless or wired, using the same communication protocol.

In the exemplary embodiment, the detection signal generated by the ultrasound module 152, in response to the received ultrasound signal, is transmitted by the communication module 159 in the oral care device 103 is transmitted to the communication module 173 of the processing module 165. The processor 169 of the processing module 165 may be programmed with functionality to analyze the detection signal generated by the ultrasound module 152.

Figure 1E:
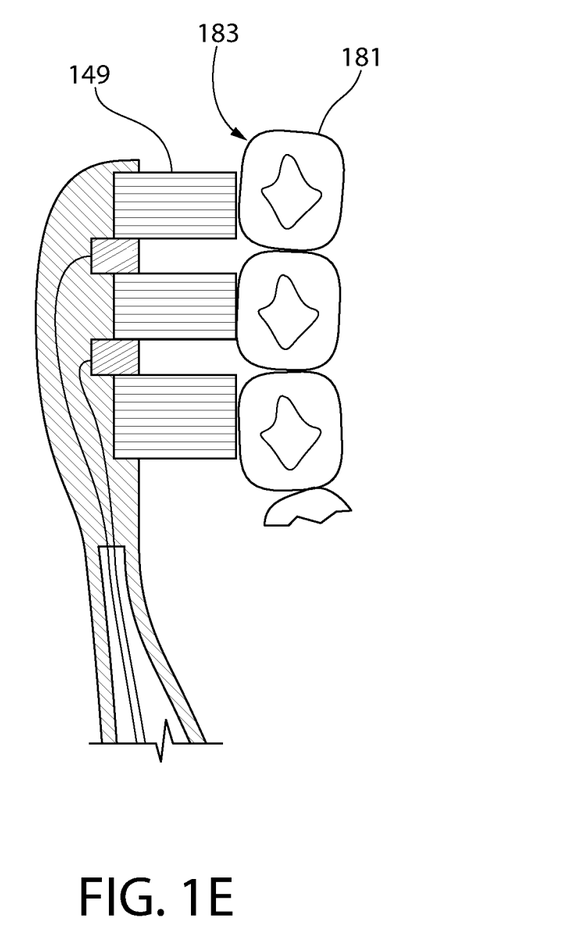
FIG. 1E illustrates a partial view of a toothbrush of the ultrasonic system of FIG. 1A.

Referring to FIGS. 1B and 1E, the oral care device 103 is positioned in an oral cavity with the bristles 149 positioned against the surface 183 of the teeth 181. During operation, the user actuates the electrical switch 143 to activate the ultrasound module 152, which causes the ultrasound transmitter 155 to begin generating the ultrasound signal and causes the ultrasound receiver 157 to begin receiving the reflected ultrasound signal and generating the detection signal. As indicated, the processor 169 analyzes the detection signal, and the programmed functionality of the processor 169 is described in greater detail below.

Figure 2A:
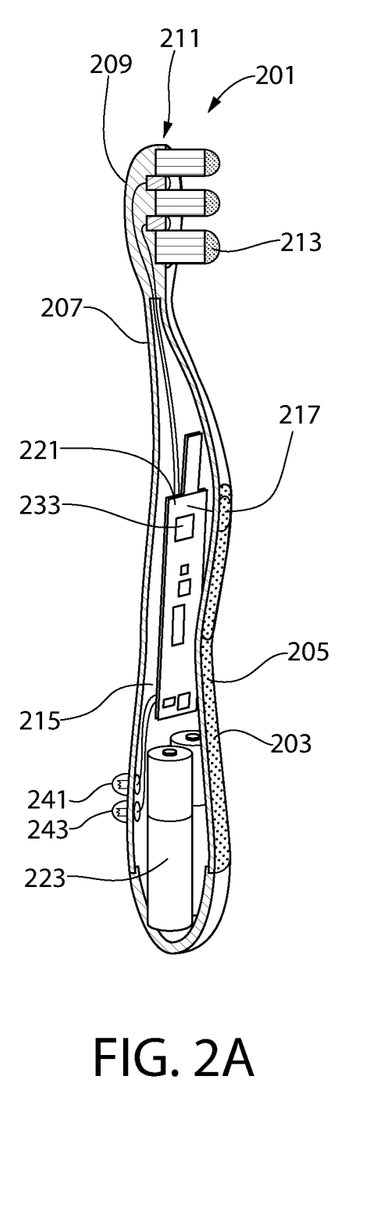
FIG. 2A illustrates an ultrasonic system in accordance with a second embodiment of the present invention.
Figure 2B:
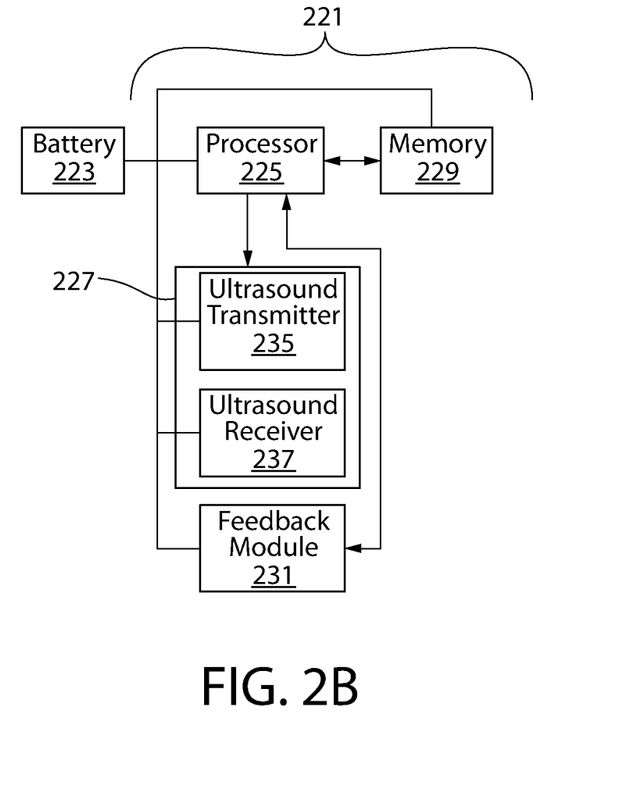
FIG. 2B schematically illustrates the electronic components of the toothbrush of FIG. 2A.

An alternative embodiment for an oral care system 201 is shown in FIG. 2. The oral care system 201 of this embodiment is entirely incorporated into the toothbrush 203. The toothbrush 203 is generally formed by a handle 205, a neck 207, and a head 209. The front surface 211 of the head 209 includes at least one teeth cleaning element, shown as a plurality of bristles 213, extending therefrom for cleaning the surfaces of teeth. The handle 205 includes a cavity 215 for housing the electronic circuitry 221 and the batteries 223, with the batteries providing power to the electronic circuitry 221. An electrical switch 217 is included as part of the handle 205 to connect and disconnect the batteries 223 to the electronic circuitry 221. The electronic circuitry 221 includes a processor 225, an ultrasound module 227, a memory 229, and a feedback module 231. The processor 225 may include an analogue to digital converter (ADC). In certain embodiments, the electronic circuitry 221 may include a separate ADC which is operationally coupled between the ultrasound module 227 and the processor 225. The ultrasound module 227 includes a controller circuit 233, an ultrasound transmitter 235, and an ultrasound receiver 237.

As with the previous embodiment, the controller circuit 233 controls operation of both the ultrasound transmitter 235 and the ultrasound receiver 237. In the embodiment shown, the ultrasound transmitter 235 is separate from the ultrasound receiver 237, and in combination the two components form an ultrasound transceiver. In certain other embodiments, the ultrasound transmitter 235 and the ultrasound receiver 237 may be integrated into a single unit to form an ultrasound transceiver. In still other embodiments, the functional aspects of the ultrasound transmitter 235 and the ultrasound transceiver 237 may be combined to form an ultrasound transceiver. The ultrasound module 227 operates in accordance with well-known principals of ultrasonography, in which an ultrasound signal is generated by the ultrasound transmitter 235 and a reflected ultrasound signal is received by the ultrasound receiver 237. The ultrasound module 227 generates a detection signal from the reflected ultrasound signal.

The feedback module 231 includes two light emitting diodes (LEDs) 241, 243, both of which are operably coupled to and controlled by the processor 225. The first LED 241 may be used as a power indicator, such that when the processor causes this LED 241 to be illuminated, the user is alerted that the ultrasound module 227 is actively generating an ultrasound signal. The second LED 243 may be used as feedback indicator, such that when the processor causes this LED 243 to be illuminated, the user is alerted that the processor has detected the presence of a biofilm on the surface of the tooth immediately adjacent the head 209 of the toothbrush 203.

In this embodiment, the detection signal generated by the ultrasound module 227, in response to the received ultrasound signal, is received by the processor 225, and the processor 225 may be programmed with functionality, described in detail below, to analyze the detection signal.

In the embodiment shown in FIGS. 2A-B, the entire functionality of the ultrasonic system is incorporated into the toothbrush 203. In comparison, the embodiment shown in FIGS. 1A-D uses a processing module 165, which is external to the oral care device 103, to analyze the detection signal. In certain other embodiments, aspects of each of the two aforementioned embodiments may be combined. For example, an ultrasonic system may include both LEDs on a toothbrush for providing feedback and use an external processing module for analyzing the detection signal.

Figure 3:
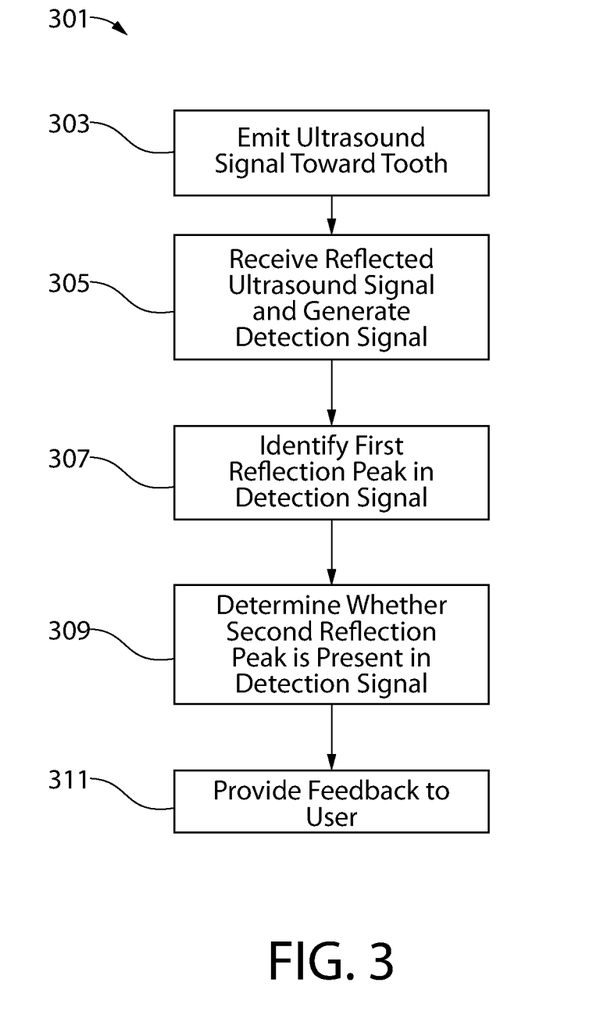
FIG. 3 illustrates a process for detecting a biofilm on the surface of a tooth in accordance with a first embodiment of the present invention.
Figure 5:
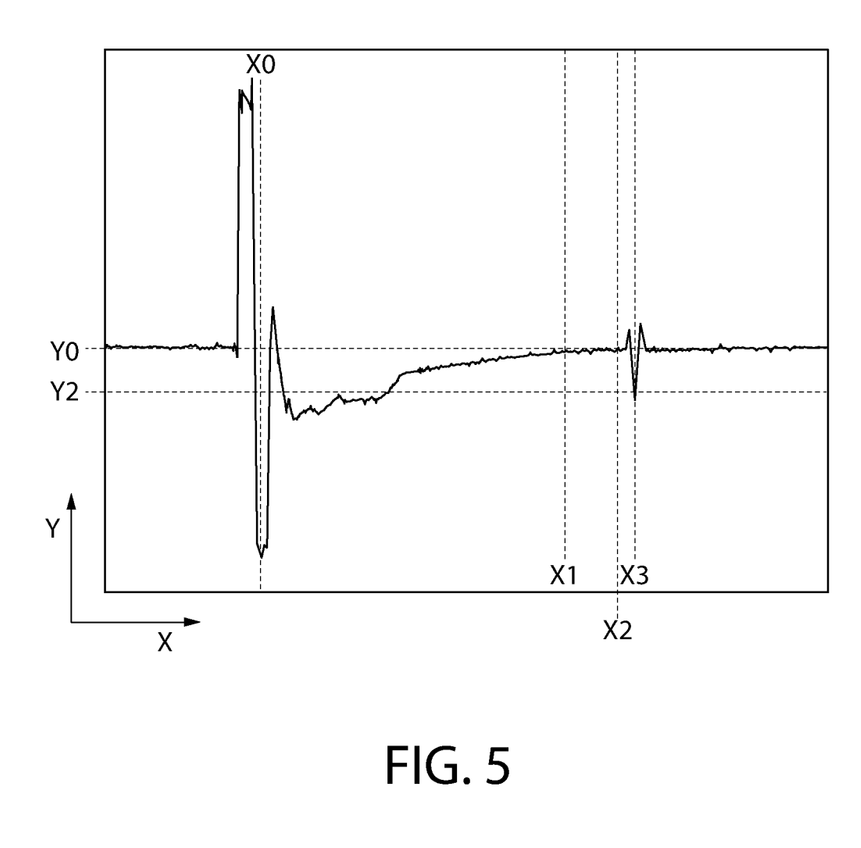
FIG. 5 is a representation of a first detection signal generated from a reflected ultrasound signal for processing to determine whether a biofilm is present on the surface of a tooth.
Figure 7:
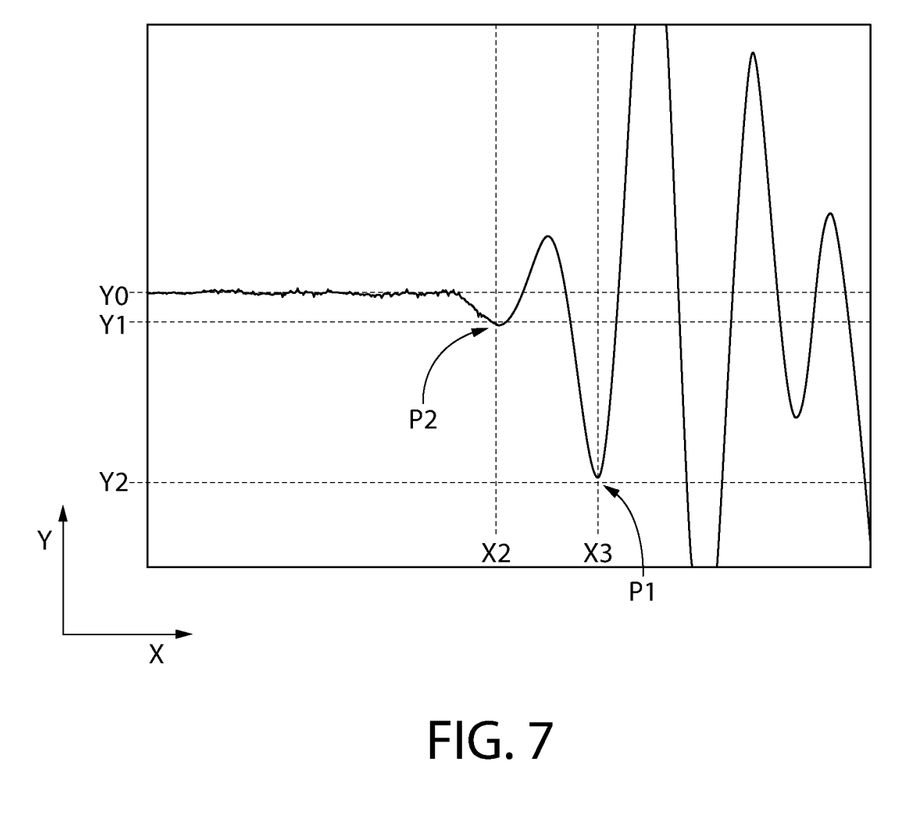
FIG. 7 is a representation of a portion of a third detection signal generated from a reflected ultrasound signal when a biofilm is present on the surface of a tooth.
Figure 8:
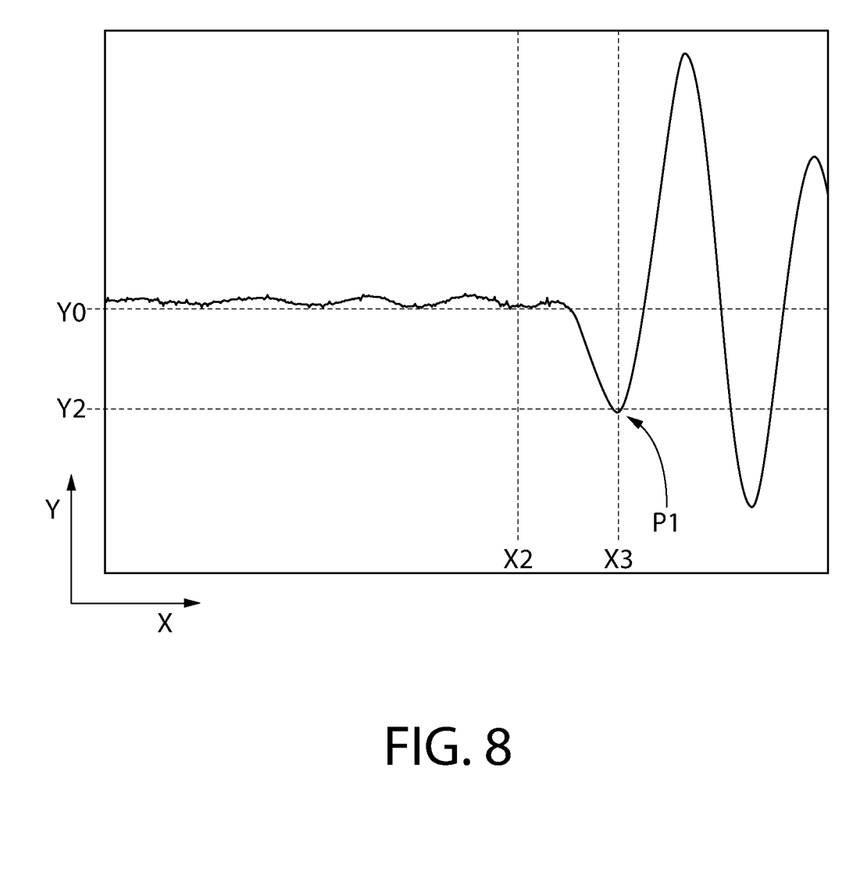
FIG. 8 is a representation of a portion of a fourth detection signal from an ultrasound transceiver.

A flowchart 301 showing a process for detecting a biofilm on the surface of a tooth is shown in FIG. 3. The process of this flowchart 301 may use one or more of the ultrasonic systems described herein, or variants or equivalents thereof, to process the generated detection signal in a non-linear manner with respect to time in order to determine whether a biofilm is present on the surface of the tooth. In addition, processing for the steps of the flowchart 301 may be carried out by the processors included as part of such ultrasonic systems. Once the toothbrush is in position adjacent a tooth, as shown in FIG. 1E, the process begins with a first step 303 of emitting an ultrasound signal, from the ultrasound transmitter, in the direction of the tooth. The next step 305 is to receive the reflected ultrasound signal and generate the detection signal. As is understood in ultrasonography, the detection signal is representative of the reflected ultrasound signal, which itself is representative of the biological structures on and in the tooth, e.g., any biofilm that is present on the tooth, the surface of the tooth, the internal structure of the tooth, etc. Next is an identification step 305 in which the first reflection peak in the detection signal is identified, i.e., the reflection peak in the detection signal that is representative of the surface of the tooth. Because information about the structure through which the ultrasound signal is passing is already known, some shortcuts may be taken during this identification step 307 as compared to traditional ultrasonography. For example, it is known that the teeth cleaning elements of the oral care device are positioned between the ultrasound transmitter and the surface of the tooth, that the surfaces of the teeth cleaning elements are typically going to be positioned at an oblique angle with respect to the direction in which the ultrasound signal is emitted, and it is also known that the tooth has a hard enamel surface, and the biofilm is a thin film that may be present on the surface of the tooth. FIG. 5 illustrates a representation of a detection signal. Along the x-axis, the time period from X0 to X1 represents the time of travel for the ultrasound signal between the ultrasound transmitter and a position less than the length of the teeth cleaning elements. Because it is known that the ultrasound signal is traveling during this time period through the bristles and possibly water, toothpaste, and/or saliva, this time period of the detection signal can be completely ignored and not processed during the identification step 307. In certain embodiments, the time period between X0 to X1 may be a time period of about 2 μsec or less. In certain other embodiments, the time period between X0 to X1 may be a time period which is dependent upon the length of the teeth cleaning elements. FIG. 7 illustrates the detection signal traveling through water as a medium, and FIG. 8 illustrates the detection signal traveling through a mixture of water, toothpaste, and saliva. By not processing the detection signal between X0 to X1, the noise generated in the detection signal by these media can be efficiently disregarded as noise.

Figure 6:
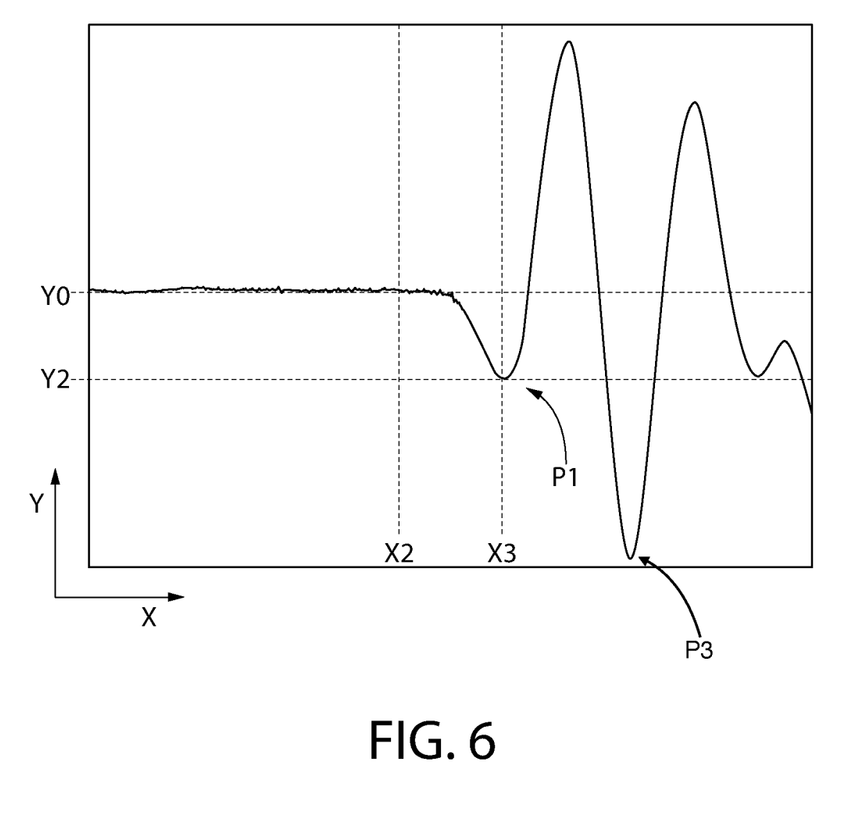
FIG. 6 is a representation of a portion of a second detection signal generated from a reflected ultrasound signal when a biofilm is not present on the surface of a tooth.

The next part of the identification step 307 is identifying the reflection peak created by the surface of the tooth. This may be done by analyzing the detection signal over time to determine how the first two reflection peaks in the detection signal, after the point X1, change over time as the oral care device is used. In FIG. 6, the first two reflection peaks are P1 and P3, and in FIG. 7, the first two reflection peaks are P1 and P2. Reflection peaks that are caused by a biofilm, such as reflection peak P2 in FIG. 7, may appear and disappear and/or show changes in amplitude and/or time position within the detection signal as the oral care device is used. In each of FIGS. 6 and 7, the reflection peak P1 represents the surface of the tooth.

Reflection peaks due to a biofilm, such as P2 in FIG. 7, will appear when a biofilm is present, disappear when the biofilm is not present, change in amplitude based on differences in distance between the ultrasound transmitter and the tooth as the oral care device is used, and change in time position within the detection signal if the thickness of the biofilm varies. In comparison, reflection peaks that are caused by the surface of the tooth, such as reflection peak P1 in FIG. 6, will change only with differences in distance between the ultrasound transmitter and the tooth as the oral care device is used—the reflection peak due to the surface of the tooth will not disappear unless the oral care device is no longer placed adjacent the tooth with the teeth cleaning elements placed against the tooth. Thus, by analyzing the detection signal for a short time period, which may be as little as 500 µsec to 10 sec, the processor is able to identify the reflection peak that is caused by the surface of the tooth. Of course, during use in certain oral cavities, such as those with an extreme amount of biofilm built up, the processor may need a longer time period to identify the reflection peak caused by the surface of the tooth.

Once the reflection peak caused by the surface of the tooth has been identified in the identification step 307, the next step is a determination step 309, in which the detection signal is analyzed to determine whether a reflection peak caused by the biofilm is present in the detection signal. Because the biofilm, if present, would be positioned between the ultrasound transmitter and the surface of the tooth, the reflection peak caused by the biofilm will be earlier in time in the detection signal than the reflection peak caused by the surface of the tooth. Also, because the biofilm is known to be a thin film, the reflection peak in the detection signal caused by the biofilm will occur during a second time period prior to the reflection peak caused by the surface of the tooth, and this second time period may be predetermined based on the average thickness of biofilm on teeth or on any other appropriate known information about biofilms on teeth. In each of FIGS. 6-8, this second time period is between X2 to X3, with X3 set at the point of the first reflection peak P1. In certain embodiments, there is a time gap left between X1 and X2 in order to clearly demarcate the two time periods. In certain other embodiments, X1 and X2 may serve as a single reference point of the detection signal.

In certain embodiments, the second time period is between about 100 nsec and 200 nsec. Time periods prior to the reflection peak caused by the surface of the tooth within this range are sufficient to detect a biofilm on the surface of a tooth up to about 150 µm thick. In certain other embodiments, the second time period is at least 10 nsec, which would enable detection of a biofilm up to about 14 µm thick. The second time period may be set at a predetermined value based upon the anticipated thickness of a biofilm. For example, a biofilm for some individuals may be expected to have an average thickness of about 2 µm, and in order to detect such biofilms, the second time period may be set to 12 nsec, which would be sufficient to detect biofilms having a thickness of up to about 8 µm. In general, the second time period may be set at a value as low as the time necessary to determine whether even a thin biofilm, even a biofilm as thin as 0.5 µm, is present on the surface of the tooth. The length of the second time period, however, should be set at a value that would allow detection of a significant percentage of biofilm widths.

Within the second time period, the process may determine whether a biofilm is present on the tooth by the presence of a reflection peak. In certain embodiments, any reflection peak within the second time period may be determined to be created by a biofilm only if the amplitude of the second reflection peak, Y1 in FIG. 7, is greater than a predetermined threshold amplitude. In certain other embodiments, changes in a reflection peak within the second time period, such as appearing, disappearing, changes in amplitude as the oral care device is used, and/or changes in relative time location, may be used to determine whether a biofilm is present on the tooth.

As will be understood from the identification step 307 and the determination step 309, the detection signal is processed in a non-linear manner with respect to time, as a later part of the detection signal is first processed in the identification step 307, and subsequently an earlier part of the detection signal is then processed in the determination step 309. The last step of the process is the feedback step 311, in which the user is provided feedback as to whether a biofilm has been detected on the surface of the tooth. The feedback can be provided by illuminating one or more LEDs, as in the embodiment of FIG. 2A, by displaying feedback on a display screen of a processing unit, such as the remote device of FIG. 1A, or by providing an audible signal to the user. The manner in which feedback is provided to the user is not limiting of the present invention, unless specifically set forth in a claim.

Figure 4:
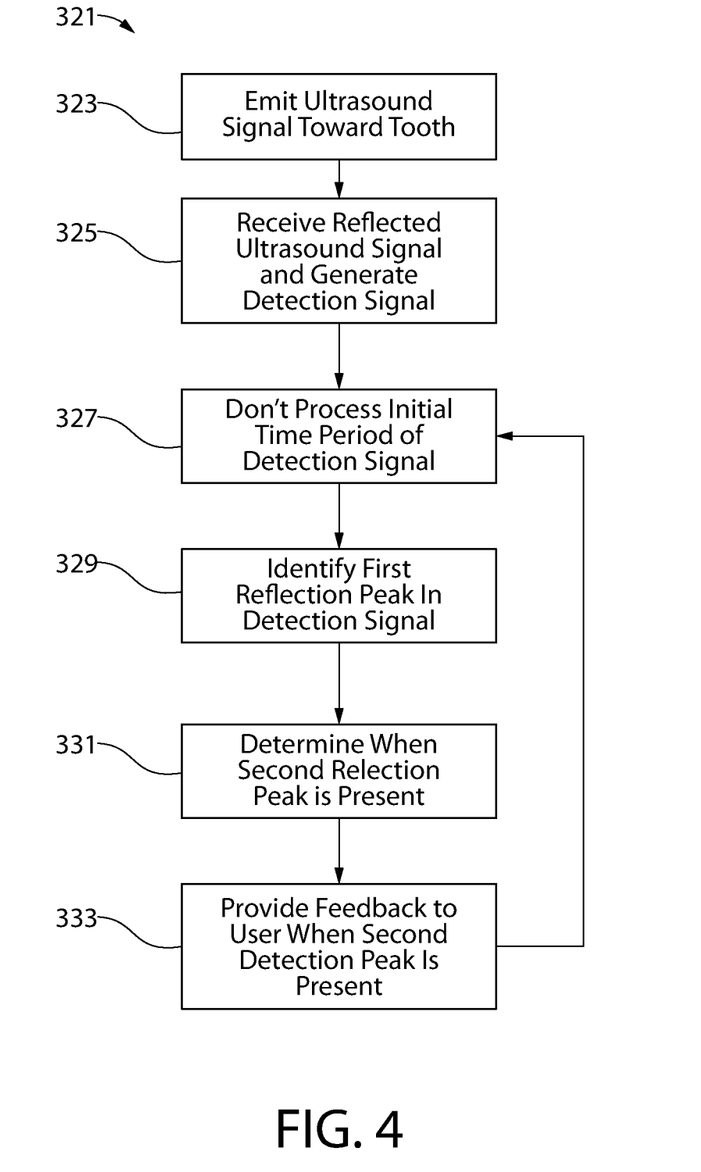
FIG. 4 illustrates a process for detecting a biofilm on the surface of a tooth in accordance with a second embodiment of the present invention.

A flowchart 321 showing a process for detecting a biofilm on the surface of teeth during an oral care routine is shown in FIG. 4. The process of this flowchart 321 may use one or more of the ultrasonic systems described herein, or variants or equivalents thereof, to process the generated detection signal in a non-linear manner with respect to time in order to determine whether a biofilm is present on the surface of the teeth. In addition, processing for the steps of the flowchart 321 may be carried out by the processors included as part of the ultrasonic systems. Once the oral care device is in position adjacent teeth the process begins with a first step 323 of emitting an ultrasound signal, from the ultrasound transmitter, in the direction of the teeth. The next step 325 is to receive the reflected ultrasound signal and generate the detection signal. Next is the initial processing step 327, in which the first part of the detection signal is ignored and not processed. As discussed above with reference to FIG. 5, this first part of the detection signal is between X0 and X1. The next step is the identification step 329, in which the reflection peak P1 in the detection signal created by the surface of the teeth is identified. In certain embodiments, as the oral care routine continues, the first reflection peak P1 in the detection signal may continue to be identified by the amplitude, Y2 in FIG. 7, in further iterations of the process. The next step is the determination step 331, in which a determination is made as to whether the detection signal includes a reflection peak P2 created by the presence of a biofilm. The identification step 329 and the determination step 331 may be performed in substantially the same manner as described above for FIG. 3. In certain embodiments, once the presence of second reflection peak P2 is determined, a ratio between the amplitude Y2 of the first reflection peak P1 and the amplitude Y1 of the second reflection peak P2 may be calculated, and this calculated ratio may be used in further iterations of the process. During the oral care routine, while the amplitudes of the reflection peaks may change due to the distance of the ultrasound transmitter from the surface of the teeth, the ratio of between the two amplitudes will remain substantially constant. This calculated ratio, therefore, provides a convenient way to determine whether the biofilm is in fact present on the surface of the teeth. The next step is the feedback step 333, in which feedback is provided to the user when the presence of a biofilm is detected on one of the teeth. The feedback may be provided using LEDs, a display screen, a speaker, and the like, to alert the user to the presence of a biofilm. After the feedback step 333 is performed, the process returns to the initial processing step 327 as the oral care routine continues.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An ultrasonic system comprising:
    an oral care device comprising:
        a head;
        a plurality of teeth cleaning elements extending from a first side of the head; and
        an ultrasound module comprising an ultrasound transceiver positioned in the head, the ultrasound transceiver configured to produce an ultrasound signal on the first side of the head and to generate a detection signal from a reflected ultrasound signal; and
    a processing module operably coupled to the ultrasound module to receive the detection signal;
    wherein the processing module comprises a programmable processor configured to process the detection signal non-linearly with respect to time by first identifying a first reflection peak representing a surface of a tooth and then determining whether a second reflection peak is present in the detection signal at a time prior to the first reflection peak, the second reflection peak representing a biofilm on the surface of the tooth.

2. The ultrasonic system of claim 1, wherein in processing the detection signal non-linearly with respect to time, the programmable processor is configured to:
    process the detection signal to identify the first reflection peak at a first time in the detection signal; and
    determine whether the second reflection peak is present in the detection signal within a first predetermined time period prior to the first time, wherein the first predetermined time period is less than about 200 ns.

3. The ultrasonic system of claim 1, further comprising a feedback module configured to provide an indication of whether the second reflection peak is present in the detection signal.

4. The ultrasonic system of claim 3, wherein the oral care device further comprises a body coupled to the head, the processing module and the feedback module being disposed within the body.

5. The ultrasonic system of claim 3, wherein the feedback module comprises at least one light emitting diode (LED), wherein the processing module configured to activate the LED to indicate when the second reflection peak is present in the detection signal.

6. The ultrasonic system of claim 1, wherein the detection signal is processed by not processing an initial part of the detection signal, the initial part of the detection signal having a second predetermined time period, wherein the second predetermined time period is about 2 μsec.

7. The ultrasonic system of claim 1, wherein the detection signal is processed by initially determining an amplitude of the first reflection peak, followed by continuing to identify the first reflection peak by the amplitude.

8. The ultrasonic system of claim 1, wherein the programmable processor is further configured to calculate an amplitude ratio between the first reflection peak and the second reflection peak.

9. The ultrasonic system of claim 1, further comprising:
    a first communication module communicably coupled to the ultrasound module and configured to transmit the detection signal;
    a processing unit comprising the processing module, a second communication module, and the feedback module, the feedback module comprising a display, the processing module communicably coupled to the second communication module and the feedback module, the second communication module configured to receive the detection signal, and the processing module configured to display the feedback to the user on the display.

10. An ultrasonic method for detecting a biofilm on a surface of a tooth, the method comprising:
    placing a head of an oral care device adjacent the surface of the tooth, the oral care device comprising a plurality of teeth cleaning elements extending from a first side of the head, such that the plurality of teeth cleaning elements are between the head and the surface of the tooth, and an ultrasound module comprising an ultrasound transceiver positioned in the head;
    generating a detection signal using the ultrasound transceiver by directing an ultrasound signal from the first side of the head toward the tooth and receiving a reflected ultrasound signal, the detection signal being generated from the reflected ultrasound signal; and
    processing, using a processing module, the detection signal non-linearly with respect to time by first identifying a first reflection peak representing a surface of a tooth and then determining whether a second reflection peak is present in the detection signal at a time prior to the first reflection peak, the second reflection peak representing a biofilm on the surface of the tooth.

11. The ultrasonic method of claim 10, wherein processing the detection signal non-linearly with respect to time comprises:
    identifying the first reflection peak at a first time in the detection signal; and
    determining whether a second reflection peak is present in the detection signal within a first predetermined time period before the first time, wherein the first predetermined time period is less than about 200 ns.

12. The ultrasonic method of claim 10, further comprising providing feedback to a user, using a feedback module, to indicate when the biofilm is present on the surface of the tooth.

13. The ultrasonic method of claim 12, wherein the feedback module comprises at least one light emitting diode (LED), and providing feedback comprises activating the LED to indicate when the biofilm is present on the surface of the tooth.

14. The ultrasonic method of claim 10, wherein identifying the first reflection peak includes not processing a beginning of the detection signal for a second predetermined time period.

15. The ultrasonic method of claim 10, wherein identifying the first reflection peak includes initially determining an amplitude of the first reflection peak, followed by continuing to identify the first reflection peak by the determined amplitude.

16. The ultrasonic method of claim 10, further comprising calculating an amplitude ratio between the first reflection peak and the second reflection peak.

17. An ultrasonic method for detecting a biofilm on a surface of teeth, the method comprising:
   moving a head of an oral care device along the surface of the teeth within an oral cavity, the oral care device comprising a plurality of teeth cleaning elements extending from a first side of the head, such that the plurality of teeth cleaning elements are between the head and the surface of the teeth, and an ultrasound module comprising an ultrasound transceiver positioned in the head;
   generating a detection signal using the ultrasound transceiver while moving the head, the ultrasound transceiver directing an ultrasound signal from the first side of the head toward the tooth and receiving a reflected ultrasound signal, the detection signal being generated from the reflected ultrasound signal;
   identifying a first reflection peak at a first time in the detection signal, using a processing module and while moving the head, the first reflection peak representing the surface of the teeth;
   determining whether a second reflection peak is present in the detection signal within a first predetermined time period before the first time, using a processing module and while moving the head, such that the second reflection peak and the first reflection peak have an amplitude ratio approximately equal to a previously calculated amplitude ratio, the second reflection peak representing a bio film on the surface of the tooth.

18. The ultrasonic method of claim 17, further comprising providing feedback to a user, using a feedback module, to indicate when the biofilm is present on the surface of the tooth.

19. The ultrasonic method of claim 17, wherein identifying the first reflection peak includes not processing a beginning of the detection signal for a second predetermined time period.

20. The ultrasonic method of claim 17, wherein identifying the first reflection peak includes initially determining an amplitude of the first reflection peak, followed by continuing to identify the first reflection peak by the determined amplitude.

* * * * *